(12) United States Patent
Haiges et al.

(10) Patent No.: US 9,309,266 B2
(45) Date of Patent: Apr. 12, 2016

(54) HIGH-PERFORMING STABLE GREEN REPLACEMENTS FOR AMMONIUM PERCHLORATE

(71) Applicant: University of Southern California, Los Angeles, CA (US)

(72) Inventors: Ralf Haiges, Los Angeles, CA (US); Karl O. Christe, Calabasas, CA (US); Cj Bigler Jones, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 135 days.

(21) Appl. No.: 14/284,929

(22) Filed: May 22, 2014

(65) Prior Publication Data

US 2014/0350266 A1    Nov. 27, 2014

Related U.S. Application Data

(60) Provisional application No. 61/826,385, filed on May 22, 2013.

(51) Int. Cl.
| | |
|---|---|
| *C06B 41/00* | (2006.01) |
| *C06B 47/10* | (2006.01) |
| *C07F 5/02* | (2006.01) |
| *C06B 49/00* | (2006.01) |
| *C07F 5/06* | (2006.01) |

(52) U.S. Cl.
 CPC ............... *C07F 5/022* (2013.01); *C06B 41/00* (2013.01); *C06B 47/10* (2013.01); *C06B 49/00* (2013.01); *C07F 5/069* (2013.01)

(58) Field of Classification Search
 CPC ......... C07F 5/022; C07F 5/069; C06B 41/00; C06B 47/10
 See application file for complete search history.

(56) References Cited

U.S. PATENT DOCUMENTS

| | | | |
|---|---|---|---|
| 7,771,549 B1 | 8/2010 | Christe et al. | |
| 2010/0307336 A1* | 12/2010 | Ni | C07F 5/022 95/127 |

\* cited by examiner

*Primary Examiner* — Joseph Kosack
(74) *Attorney, Agent, or Firm* — Brooks Kushman P.C.

(57) ABSTRACT

A highly energetic, high-oxygen carrier suitable as high-performing green replacement for ammonium perchlorate includes halogen-free ionic salts consisting of fuel cations and over-oxidized anions containing multiple nitro- or nitromethyl-substituted azolyl ligands. The over-oxidized anions include a central atom selected from the group consisting of boron, aluminum, or gallium. Characteristically, the carrier has sufficient amounts of oxygen for complete or near complete combustion of the over-oxidized anions, the fuel cations, metal additives and binders.

38 Claims, 6 Drawing Sheets

HIGH-PERFORMING STABLE GREEN REPLACEMENTS FOR AMMONIUM PERCHLORATE

CROSS-REFERENCE TO RELATED APPLICATIONS

This application claims the benefit of U.S. provisional application Ser. No. 61/826,385 filed May 22, 2013, the disclosure of which is hereby incorporated in its entirety by reference herein.

STATEMENT REGARDING FEDERALLY SPONSORED RESEARCH OR DEVELOPMENT

The invention was made with Government support under Contract Nos. N00014-01-0393 and N00014-12-1-0555 awarded by the Office of Naval Research. The Government has certain rights to the invention.

TECHNICAL FIELD

In at least one aspect, the present invention relates to high-oxygen carriers that do not contain halogens.

BACKGROUND

Ammonium perchlorate (AP) is the most commonly used high-oxygen carrier in propellants, explosives, pyrotechnics and ammunitions. Ammonium perchlorate is the major oxidizer used in composite solid rocket propellants carrying sufficient amounts of oxygen to oxidize not only the ammonium cation, but also substantial amounts of aluminum powder (about 15 weight %), binder (about 12 weight %), and curing agent (about 2 weight %). The performance of such composite solid rocket propellant formulations is measured in terms of their specific impulse ($I_{sp}$) which for a typical ammonium perchlorate based propellant is about 265 sec. Besides providing a high $I_{sp}$, the high-oxygen carrier in such composite propellant formulations must fulfill additional requirements. It must be hydrolytically stable to allow processing and storage of the propellant in the atmosphere, be compatible with the other ingredients used in the formulation, and must be relatively insensitive to impact, friction and heat.

Ammonium perchlorate is commercially produced on a very large scale electrochemically by anodic oxidation of chlorate. For example, the production of ammonium perchlorate at the Henderson Nev. facilities alone amounted to 76 million pounds per year in 1998. The major drawbacks of the use of ammonium perchlorate in propellant formulations are the generation of HCl as a combustion product giving rise to huge amounts of acidic rain, and its high toxicity to humans causing thyroid problems already at very low concentrations at the ppb level in drinking water. As a result, the large scale use of ammonium perchlorate in propellants is facing increasing scrutiny and likely congressional actions to restrict its use. Such actions have as yet not been taken due to the lack of a suitable high-performing green replacement. The problem of finding a suitable green replacement for ammonium perchlorate has been pursued for more than a century but so far has not been solved. Thus, there is an urgent need to find a green replacement for ammonium perchlorate in view of the global need for using high-performing solid propellant rockets for the launch of communication satellites, strategic missiles and space exploration missions.

Potential replacements for ammonium perchlorate should be environmental friendly (i.e., green), high-performing, thermally and hydrolytically stable. Such replacements are desirably highly energetic high-oxygen carriers. In general, the sensitivity of an energetic material increases sharply with its energy content. Therefore, finding highly energetic materials exhibiting low sensitivity is very difficult and rare. Similarly, high thermal stability generally requires very strong bonds which decrease the energy content, and it is difficult to find highly energetic materials which at the same time possess high thermal stability. Moreover, for large scale use, as in the solid propellant boosters for the major launch systems, it is imperative that the cost of the propellant ingredients is low, and simple high yield methods for their production can be devised. While some of these requirements had previously been incorporated into some energetic materials, the successful combination of all of these principles in a single compound presents an enormous challenge and has never been achieved before. For example, the synthesis of energetic ionic liquids derived from nitrato- or perchlorato-substituted borate, aluminate, phosphate or titanate salts has previously been disclosed by Christe and Drake in U.S. Pat. No. 7,771, 549. However, the compounds of this patent are low-melting ionic liquids of insufficient oxygen balance, hydrolytical and thermal stability.

Accordingly, there is a need for a practical high-performing green replacement for ammonium perchlorate which can meet all the above requirements.

SUMMARY

The present invention solves one or more problems of the prior art by providing, in at least one embodiment, a highly energetic, high-oxygen carrier suitable as a high-performing green replacement for ammonium perchlorate. The high-oxygen carrier includes halogen-free ionic salts consisting of fuel cations and over-oxidized anions and multiple nitro-substituted azolyl ligands. The over-oxidized anions include a central atom selected from the group consisting of boron, aluminum, or gallium. Characteristically, the carrier has sufficient amounts of oxygen for complete or near complete combustion of the over-oxidized anions, the fuel cations, metal additives and binders.

In another embodiment, a highly energetic, high-oxygen carrier suitable as high-performing green replacement for ammonium perchlorate is provided. The high-oxygen carrier includes a halogen-free ionic salt having a fuel cation and an over-oxidized anion described by formula I:

wherein:
$X_1, X_2, X_3, X_4$ are each independently C—R or N;
R is H, $NO_2$ or —$C(NO_2)_3$ with the proviso that 0, 1, 2, or 3 of $X_1, X_2, X_3, X_4$ are N and at least one of $X_1, X_2, X_3, X_4$ includes $NO_2$ or $C(NO_2)_3$; and
M is boron, aluminum, or gallium. Characteristically, the carrier has sufficient amounts of oxygen for complete or near complete combustion of the over-oxidized anion, the fuel cation, metal additives and binders.

In still another embodiment, a method of preparing highly energetic, high-oxygen carriers is provided. The method includes a step of reacting a metal or semimetal compound including a moiety having formula $ML_n$ with a nitro- or nitromethyl-substituted azole having formula II

II to form a first salt having a first cation and an over-oxidized anion described by formula I such that molecular hydrogen or a $C_{1-12}$ alkane is evolved:

I wherein:
$X_1, X_2, X_3, X_4$ are each independently C—R or N;
R is H, $NO_2$ or —$C(NO_2)_3$ with the proviso that 0, 1, 2, or 3 of $X_1, X_2, X_3, X_4$ are N and at least one of $X_1, X_2, X_3, X_4$ includes $NO_2$ or $C(NO_2)_3$;
M is boron, aluminum, or gallium;
L are independently a hydrogen atom or a $C_{1-12}$ alkyl ligand; and
n is 1 to 4.

In yet another embodiment, a method for forming an ammonium tetrakis-nitroazolylborate salt is provided. The method includes a step of reacting a tris-nitroazolyl borane having formula III with an ammonium nitroazolate salt having formula IV:

wherein:
$X_1, X_2, X_3, X_4$ are each independently C—R or N;
R is H, $NO_2$ or —$C(NO_2)_3$ with the proviso that 0, 1, 2, or 3 of $X_1, X_2, X_3, X_4$ are N and at least one of $X_1, X_2, X_3, X_4$ includes $NO_2$ or $C(NO_2)_3$; and
$M^+$ is ammonium.

Advantageously, the embodiments and variations disclosed herein provide green, high-performing, thermally and hydrolytically stable, highly energetic high-oxygen carriers of low impact and friction sensitivity which can be prepared at moderate cost in high yield and purity by simple processes from readily available starting materials. The goal of environmental friendliness is achieved by avoiding the incorporation of halogen and other elements which can give rise to toxicity to the compounds. The required high oxygen balance is achieved by using complex anions containing a benign low-atomic weight central atom and multiple ligands each carrying nitro or nitromethyl groups thus resulting in a positive oxygen balance. The necessary energy content is created by using high-nitrogen heterocyclic azolyl ligands because nitrogen-nitrogen bonds are weaker and easier to break than carbon-carbon bonds. Furthermore, the incorporated nitrogen atoms generate triple bonded dinitrogen as a combustion product resulting in a high energy release and reducing the amount of oxygen needed for the combustion of the ligand. Since low molecular weights of the combustion products result in increased $I_{sp}$ values, atoms of the short and the first long period of the periodic system are preferentially used for the construction of the anions and cations. To achieve hydrolytic stability, the central atom of the anion is coordinatively saturated to preempt attack by water molecules. This goal is achieved by the use of boron or aluminum.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Abbreviations:

"DNT" refers to dinitrotriazolyl groups such as 3,5-dintro-1H-1,2,4-triazolyl.

"HDNT" refers to dinitrotriazole such as 3,5-dintro-1H-1,2,4-triazole.

"NTz" refers to nitrotetrazolyl groups such as 5-nitro-2H-tetrazolyl.

"HNTz" refers to nitrotetrazole such as 5-nitro-2H-tetrazole.

"TNTz" is trinitromethyltetrazolyl such as 5-trinitromethyl-2H-tetrazolyl.

"HTNTz" is trinitromethyltetrazole such as 5-trinitromethyl-2H-tetrazole.

"Me" is methyl.

The term "high-oxygen" as used herein refers to compounds that include nitro groups and are able to oxidize cations having oxidizable bonds with the evolution of additional oxygen in a balanced equation.

The term "fuel cation" as used herein refers to cations that have oxidizable bonds. Examples of such cations include, but are not limited to, $NH_4^+$, $N_2H_5^+$, $N_2H_6^{2+}$, $NH_3OH^+$, or $H_2NC(NH_2)NH_2^+$.

In an embodiment, a highly energetic, high-oxygen carrier suitable as high-performing green replacement for ammonium perchlorate is provided. The high-oxygen carrier includes halogen-free ionic salts consisting of fuel cations and over-oxidized anions with nitro- or nitromethyl-substituted azolyl ligands. The over-oxidized anions include a central atom selected from the group consisting of boron, aluminum, or gallium. Characteristically, the carrier has sufficient amounts of oxygen for complete or near complete combustion of the over-oxidized anions, the fuel cations, metal additives and binders.

In another embodiment, a highly energetic, high-oxygen carrier suitable as high-performing green replacement for ammonium perchlorate is provided. The high-oxygen carrier includes a halogen-free ionic salt having a fuel cation and an over-oxidized anions described by formula I:

wherein:

$X_1$, $X_2$, $X_3$, $X_4$ are each independently C—R or N;

R is H, $NO_2$ or —$C(NO_2)_3$ with the proviso that 0, 1, 2, or 3 of $X_1$, $X_2$, $X_3$, $X_4$ are N and at least one of $X_1$, $X_2$, $X_3$, $X_4$ includes $NO_2$ or $C(NO_2)_3$; and M is boron, aluminum, or gallium, the carrier having sufficient amounts of oxygen for complete or near complete combustion of the over-oxidized anion, the fuel cation, metal additives and binders. In one useful refinement, M is boron. In another useful refinement, M is aluminum. Typical fuel cations employed are derived from the family of nitrogen/hydrogen compounds. Examples of the fuel cations include ammonium cations and substituted ammonium cations such as $NH_4^+$, $N_2H_5^+$, $N_2H_6^{2+}$, $NH_3OH^+$, or $H_2NC(NH_2)NH_2^+$. Variations of the anion/cation combinations can be used to maximize the performance and physical properties, such as the melting point, density and thermal stability, of the resulting salts. For example, this type of crystal engineering is known to result either in high melting solids for solid propellant ingredients by the use of small hard cations or in low melting ionic liquids for liquid monopropellant applications by the use of large soft cations. As in the case of the anions, these cations are environmentally benign and contain only green elements.

Figure 1A:
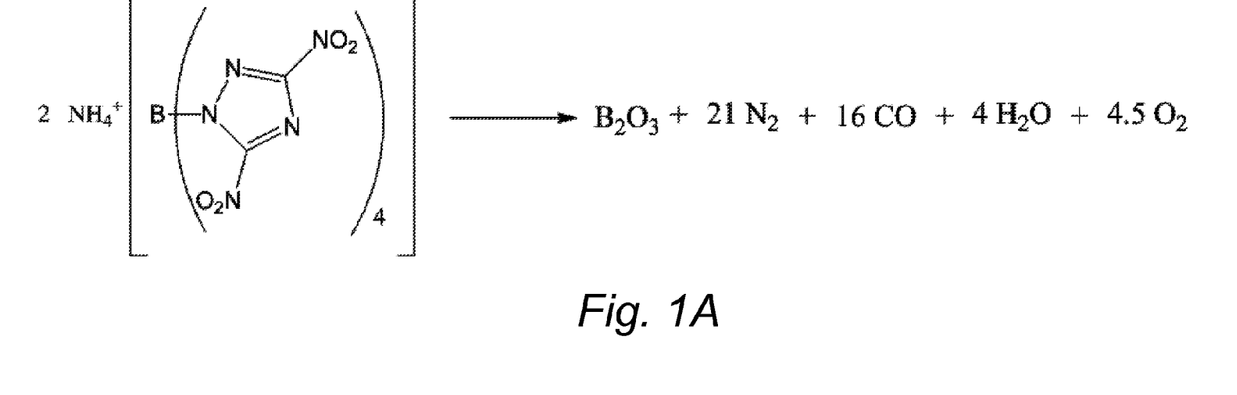
FIG. 1A provides an oxygen balanced equation for ammonium tetrakis-(3,5-dinitro-1H-1,2,4-triazolyl)borate.
Figure 1B:
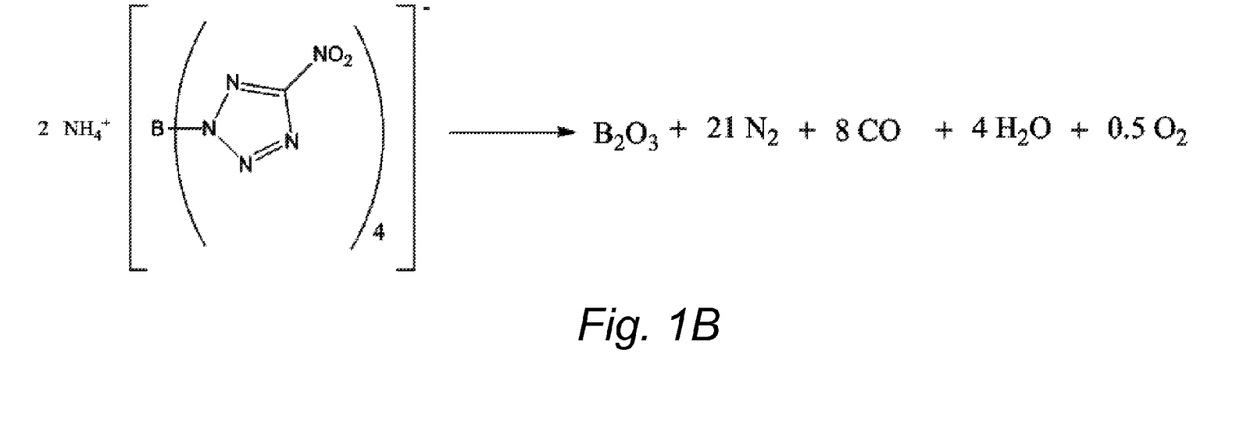
FIG. 1B provides an oxygen balanced equation for ammonium tetrakis(5-nitro-2H-tetrazolyl)borate.
Figure 1C:
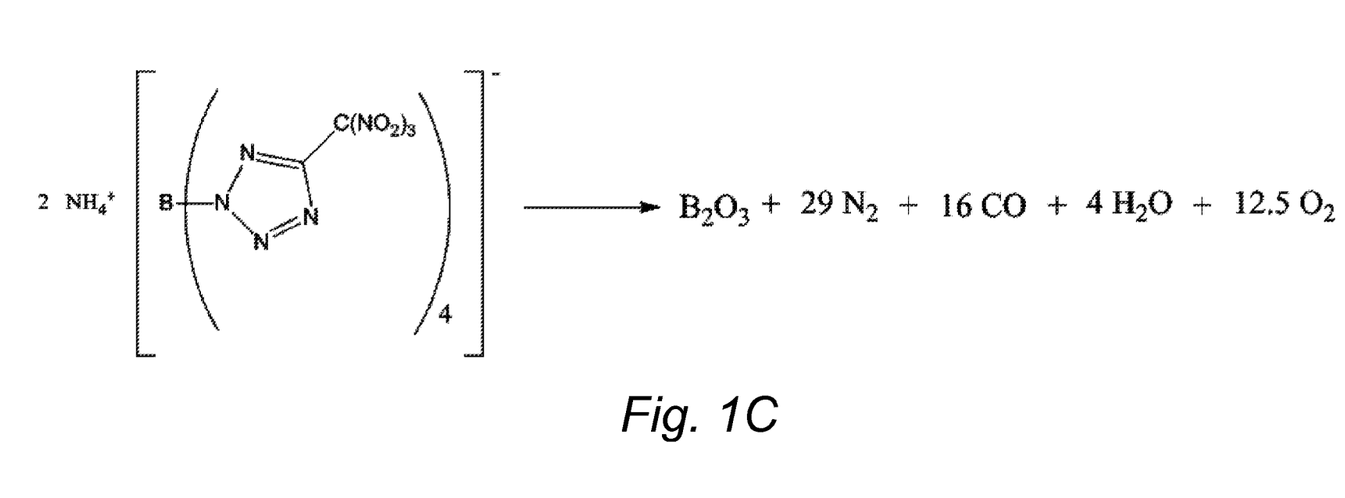
FIG. 1C provides an oxygen balanced equation for ammonium tetrakis(5-(trinitromethyl)-2H-tetrazolyl)borate.
Figure 2:
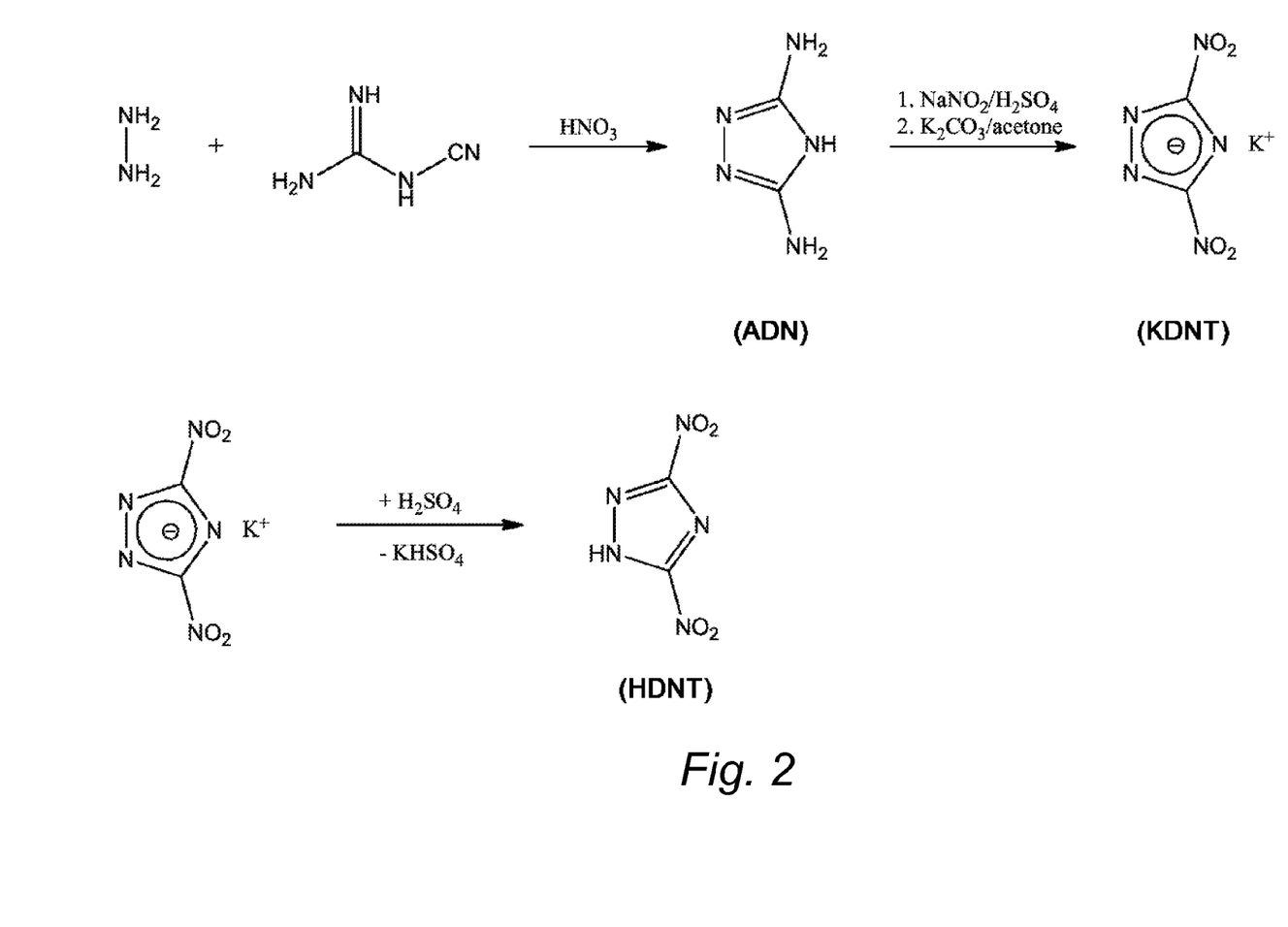
FIG. 2 provides an example of a synthetic scheme for forming 3,5-dinitro-1H-1,2,4-triazole.
Figure 3:
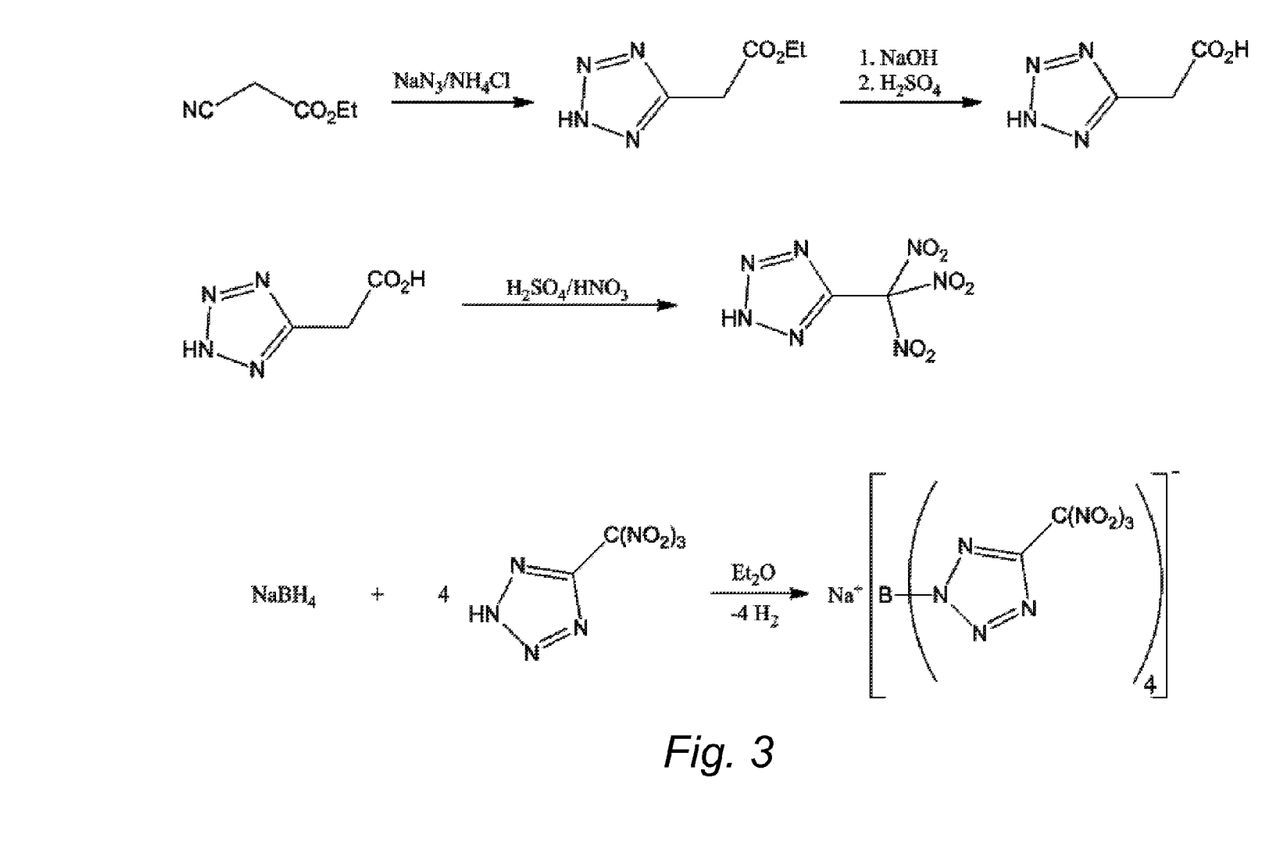
FIG. 3 provides an example of a synthetic scheme for forming 5-trinitromethyl-2H-tetrazole and subsequent reaction with sodium borohydride.

Important benefits of the materials of the present invention are their high performance as propellants approximating those of ammonium perchlorate based formulations, their low impact and friction sensitivities allowing safe preparation, handling and storage, and their hydrolytic stability permitting the processing under ambient conditions and long term storage. A typical example for the excellent performance characteristics of the compounds of the present invention is ammonium tetrakis-(3,5-dinitro-1H-1,2,4-triazolyl)borate. It has an excellent oxygen balance carrying an extra 2.25 mol of $O_2$ per mole as illustrated in FIG. 1A. Application of the Cheetah v7.0 performance calculation program demonstrates that the maximized specific impulse of its aluminized formulation containing hydroxy terminated polybutadiene as a binder (260 sec) is comparable to that of the corresponding AP based propellant. The impact and friction sensitivities of the neat compound are 13 J and >360 N, respectively, and similar to those of AP which has an impact sensitivity of 15 J and is also insensitive to friction. Furthermore, it is hydrolytically stable and can be recovered from aqueous solutions unchanged. These properties and their green nature render the materials of the present invention superior to the presently used environmentally harmful ammonium perchlorate based systems. Similarly, FIG. 1B provides an oxygen balanced equation for ammonium tetrakis(5-nitro-2H-tetrazolyl)borate and FIG. 1C provides an oxygen balanced equation for ammonium tetrakis(5-(trinitromethyl)-2H-tetrazolyl)borate.

As is apparent from formula (I), the over-oxidized anion includes a central atom M surrounded by four substituted azolyl ligands described by formula:

where the wavy line represents the point of attachment to M. In a refinement, the substituted azolyl ligands include a nitro-substituted azolyl ligand selected from the group consisting of 3,5-dinitro-1H-1,2,4-triazolyl, 5-nitro-3-(trinitromethyl)-1H-1,2,4-triazolyl, 5-(trinitromethyl)-2H-tetrazolyl, 5-nitro-2H-tetrazolyl, 3,4,5-trinitro-1H-pyrazolyl, 2,4,5-trinitro-1H-imidazolyl, and combinations thereof. Moreover, examples of over-oxidized anions include, but are not limited to, tetrakis(3,5-dinitro-1H-1,2,4-triazolyl)borate, tetrakis(5-nitro-3-(trinitromethyl)-1H-1,2,4-triazolyl)borate, tetrakis(5-(trinitromethyl)-2H-tetrazolyl)borate, tetrakis(5-nitro-2H-tetrazolyl)borate, tetrakis(3,4,5-trinitro-1H-pyrazolyl)borate, tetrakis(2,4,5-trinitro-1H-imidazolyl)borate, tetrakis(5-nitro-2H-tetrazolyl)borate, tetrakis(5-(trinitromethyl)-2H-tetrazolyl)borate, tetrakis(3,5-dinitro-1H-1,2,4-triazolyl)aluminate, tetrakis(5-nitro-3-(trinitromethyl)-1H-1,2,4-triazolyl)aluminate, tetrakis(5-(trinitromethyl)-2H-tetrazolyl)aluminate, tetrakis(5-nitro-2H-tetrazolyl)aluminate, tetrakis(3,4,5-trinitro-1H-pyrazolyl)aluminate, tetrakis(2,4,5-trinitro-1H-imidazolyl)aluminate, tetrakis(5-nitro-2H-tetrazolyl)aluminate, and tetrakis(5-(trinitromethyl)-2H-tetrazolyl)aluminate.

In still another embodiment, a method of preparing highly energetic, high-oxygen carriers is provided. The method includes a step of reacting a metal or semimetal compound including a moiety having formula $ML_n$ with nitro-substituted azoles having formula II:

to form a first salt having a first cation and an over-oxidized anion described by formula I such that molecular hydrogen or a $C_{1-12}$ alkane is evolved:

wherein:
$X_1$, $X_2$, $X_3$, $X_4$ are each independently C—R or N;
R is H, $NO_2$ or —$C(NO_2)_3$ with the proviso that 0, 1, 2, or 3 of $X_1$, $X_2$, $X_3$, $X_4$ are N and at least one of $X_1$, $X_2$, $X_3$, $X_4$ includes $NO_2$ or $C(NO_2)_3$;
M is boron, aluminum, or gallium;
L are independently a hydrogen atom or a $C_{1-12}$ alkyl ligand; and
n is 1 to 4. In one useful refinement, M is boron. In another useful refinement, M is aluminum.

An aspect of the present embodiment is the ease with which the disclosed materials can be prepared in high yields from commercially available starting materials. Low-cost production processes are very crucial for their large scale usage in practical systems. Most materials of the present invention can be prepared by scalable processes using standard nitration literature procedures for the syntheses of the azole starting materials and the subsequent reactions with either hydrides or alkyl compounds of boron or aluminum (FIGS. 2-5). For example, the 3,5-dinitro-1H-1,2,4-triazole (HDNT) is a white, wax-like solid which sublimes at 110° C. in vacuo, has a density of 1.92 g/cm³ at 123 K and decomposes at 168° C., and has impact and friction sensitivities of 35 J and 144 N, respectively. Its hydrogen atom is acidic and readily reacts with the hydridic hydrogens of alkali metal $BH_4^-$ salts or ammonia borane in diglyme at elevated temperature under quantitative hydrogen evolution.

In a refinement, the metal or semi-metal compound includes boron or aluminum. An example of such a compound is ammonia borane. Particularly useful metal or semi-metal compounds include $BH_4^-$. In a refinement, the metal or semi-metal compound is an alkali metal $BH_4^-$ salt. In a further refinement, the alkali metal $BH_4^-$ salt includes an alkali metal selected from the group consisting of lithium, sodium, potassium. Examples for the alkali metal $BH_4^-$ salts include alkali metal borohydrides.

wherein:
$M_c$ is a counter-ion (e.g., Li, Na, K, etc);
HAZ is a compound having formula 2;

AZ is as set forth above; and
n is an integer from 1 to 4. The present method is further exemplified by the following schemes:

In a refinement, ammonia borane is reacted with acidic hydrogen atoms of nitroazoles under dihydrogen evolution to form an ammonium tetrakis-nitroazolylborate salt as exemplified by the following:

Typically, the reaction of the present embodiment takes place in a solvent, and in particular, an aprotic solvent. Suitable solvents include C2-C12 alkyl ethers and polyethers such as dimethoxyethane (glyme) or 1-methoxy-2-(2-methoxyethoxy)ethane (diglyme).

Figure 4A:
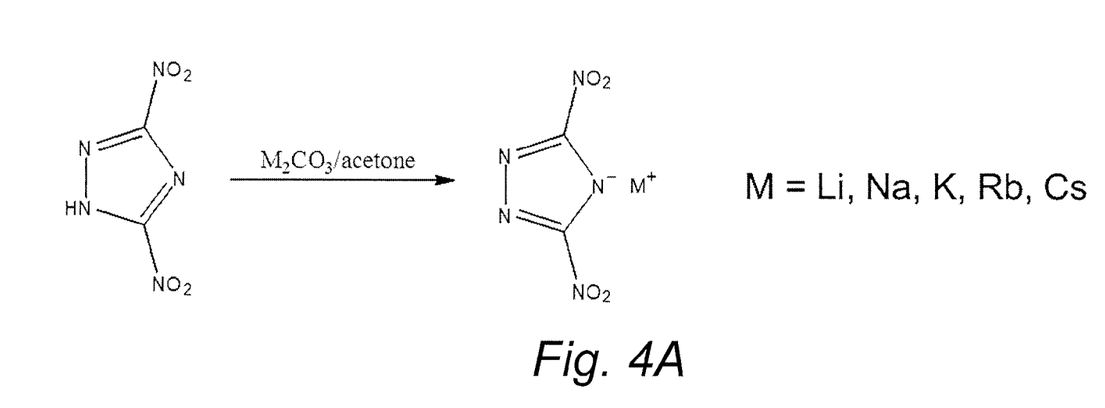
FIGS. 4A-C illustrate the reaction of 3,5-dinitro-1H-1,2,4-triazole with various bases to form the corresponding salts.
Figure 4B:
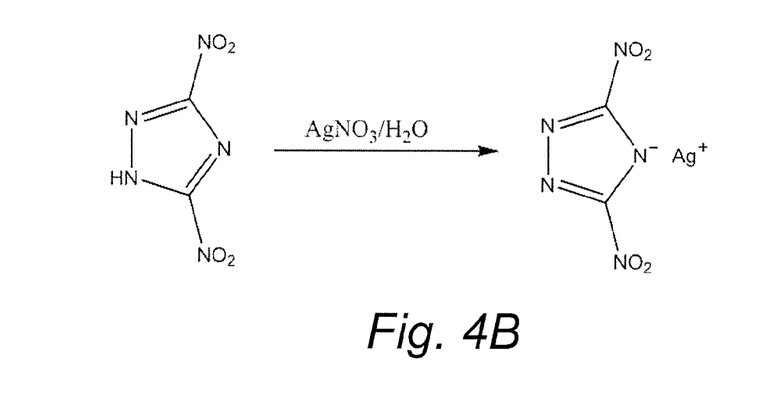
Figure 4C:
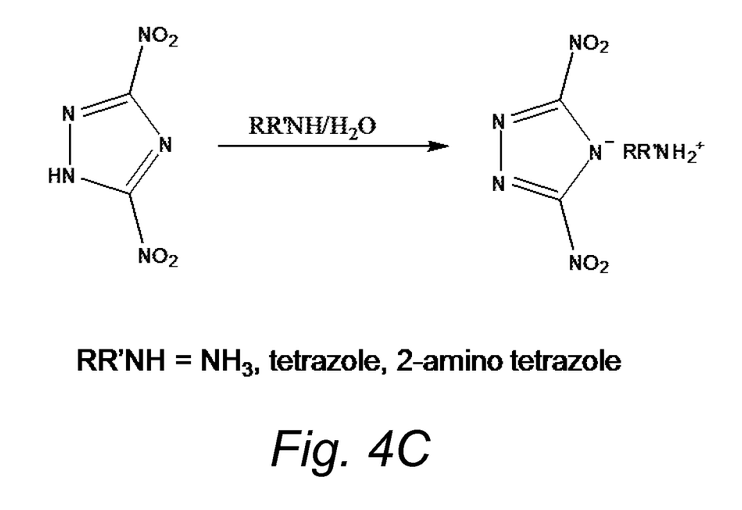

In another variation, when the first salt does not include a fuel cation, exchange of the cation is preformed. For example, the first salt is subjected to an ion exchange reaction to replace the first cation with a fuel cation. In one refinement, the first salt is contacted with ion exchange resins to form an ammonium tetrakis-nitroazolylborate salt. For example, an alkali metal tetrakis-nitroazolylborate salt can be reacted by double ion-exchange metathesis to form an ammonium salt. The ion exchange reaction is illustrated by the following scheme using, for example, an Amberlyst 15 ion-exchange resin column in $CH_3CN$ solution:

In yet another embodiment, a method for forming an ammonium tetrakis-nitroazolylborate salt is provided. The method includes a step of reacting a tris-nitroazolyl borane having formula III with an ammonium nitroazolate salt having formula IV:

wherein:
$X_1$, $X_2$, $X_3$, $X_4$ are each independently C—R or N;

R is H, $NO_2$ or —$C(NO_2)_3$ with the proviso that 0, 1, 2, or 3 of $X_1$, $X_2$, $X_3$, $X_4$ are N and at least one of $X_1$, $X_2$, $X_3$, $X_4$ includes $NO_2$ or $C(NO_2)_3$; and $M_1^+$ is an ammonium cation or a substituted ammonium cation as set forth above. FIGS. 4A-C provide examples of reactions for forming the salts having formula IV. The method of the present embodiment can be performed in the presence of a salt that includes an oxidizable cation as shown by the following reactions:

$BCl_3 + M_1Cl + nNaDNT \rightarrow M_1^+[BCl_{(4-n)}(DNT)_n]^- + nNaCl$ $N(CH_3)_4Cl + BCl_3 + nKDNT \rightarrow [N(CH_3)_4]^+[BCl_{(4-n)}(DNT)_n]^- + nKDNT$ It should be appreciated that the fuel cations of the present invention are not restricted to the ammonium ion and that other suitable cations derived from the nitrogen/hydrogen family can be substituted for $NH_4^+$. Typical examples are $N_2H_5^+$, $N_2H_6^{2+}$, $NH_3OH^+$, and $H_2NC(NH_2)NH_2^+$. Exchange of the alkali metal or ammonium cations in their nitroazolylborate salts for one of the above listed nitrogen/hydrogen based cations $M_1^+$ can be accomplished by the use of either ion-exchange resins, metathetical reactions, or the reaction of $M^+DNT^-$ with the $B(DNT)_3$ parent molecule which could be prepared by the reaction of, for example, $Na[B(DNT)_4]$ with strong acids. These ion replacements reactions are shown schematically by the following equations.

$Na[B(DNT)_4] + M_1^+\text{-resin} \rightarrow M_1^+[(DNT)_4]^- + Na^+\text{-resin}$ $Na[B(DNT)4] + M_1^+SbF_6^- \rightarrow M_1^+[B(DNT)_4]^- + NaSbF_6$ $B(DNT)_3 + M_1^+DNT^- \rightarrow M_1^+[B(DNT)_4]^-$ where $M_1^-$ is an ammonium cation or a substituted ammonium cation as set forth above. Selection of suitable cation/anion combinations provides the opportunity to fine-tune the properties of the desired products.

The following examples illustrate the various embodiments of the present invention. Those skilled in the art will recognize many variations that are within the spirit of the present invention and scope of the claims.

Example 1

Sodium tetrakis(3,5-dinitro-1H-1,2,4-triazolyl)borate: Under anhydrous conditions and a stream of dry nitrogen, 6.36 g (40.0 mmol) 3,5-dinitro-1H-1,2,4-triazole and 37.8 mg (10.0 mmol) sodium borohydride were loaded into a dry 250 mL three-necked round bottom flask that was equipped with a TEFLON™ coated stirring bar, an addition funnel and a reflux condenser. While stirring, 50 mL of anhydrous 1-methoxy-2-(2-methoxyethoxy)ethane (diglyme) was carefully added through the addition funnel. Immediately, hydrogen gas was evolved and the reaction mixture turned yellow-orange. When the addition was complete, the addition funnel was replaced by a stopper. The mixture was heated to 50° C. for three hours and then to 110° C. for an additional 24 hours. The obtained orange solution was allowed to cool to ambient temperature and all volatiles were pumped-off in vacuo. Subsequent evacuation to a constant weight over a period of 48 hours resulted in a yellow solid of sodium tetrakis(3,5-dinitro-1H-1,2,4-triazolyl)borate, 8.5 g. Decomposition temperature: 167.6° C. (TGA, weight loss: 69.4%), density: 1.80 g/cm³ at 20° C.

Example 2

Potassium tetrakis(3,5-dinitro-1H-1,2,4-triazolyl)borate: A 150 mL glass ampule equipped with a grease-free high-vacuum PTFE valve and a TEFLON™ coated stir bar was flamed-out under vacuum. Inside the dry-box, the ampule was loaded with 588 mg (4.00 mmol) 3,5-dinitro-1H-1,2,4-triazole and 53.9 mg (1.00 mmol) potassium borohydride. The ampule was connected to a vacuum line, evacuated and cooled to –196° C. About 5 mL of dry dimethoxyethane was slowly condensed into the ampule. The ampule was closed and allowed to warm to ambient temperature. As soon as the solvent melted and contacted the solid mixture at the bottom of the ampule, gas evolution started. The mixture was then stirred for about 30 minutes at ambient temperature. The clear, light yellow solution was cooled to –196° C., and 1.5 mmol of evolved hydrogen (determined by p, V, T measurements) were pumped off. The ampule was closed off and heated to 60° C. while stirring. After 3 hours, an orange solution was obtained and the temperature was first raised to 80° C. and, after an additional 8 hours, to 110° C. After 24 hours, the solution was allowed to cool to ambient temperature and then cooled to –196° C. An additional 2.50 mmol of evolved hydrogen (determined by p, V, T measurements) was pumped off. The reaction mixture was allowed to warm to ambient temperature. Subsequent evacuation to a constant weight over 24 hours resulted in an orange solid of potassium tetrakis(3,5-dinitro-1H-1,2,4-triazolyl)borate, 1.0 mmol. Decomposition temperature: 165° C. (DTA).

Example 3

Ammonium tetrakis(3,5-dinitro-1H-1,2,4-triazolyl)borate: In a 500 mL beaker flask, 48.8 g (230 meq) of Amberlyst-15 ion-exchange resin (H⁺ form) was suspended in a solution of about 100 mL of water and 100 mL of 28% ammonium hydroxide, and stirred for about 20 minutes. The mixture was filtered through a Buchner funnel and the resin was thoroughly washed with plenty of water and rinsed with 200 mL of methanol. The $NH_4^-$-form of the ion-exchange resin was dried in vacuo at ambient temperature.

A solution of 10.0 g (15.0 mmol) sodium tetrakis(3,5-dinitro-1H-1,2,4-triazolyl)borate in 100 mL anhydrous acetonitrile was passed through a column containing 30 g (135 meq) of the anhydrous ammonium loaded Amberlyst-15 ion-exchange resin and the eluent collected in a 500 mL Schlenk flask. The column was washed with an additional 100 mL of anhydrous acetonitrile. Subsequent evacuation of the vessel containing the combined yellow eluents to a constant weight over 24 hours resulted in a yellow, glass-like solid of ammonium tetrakis(3,5-dinitro-1H-1,2,4-triazolyl)borate, 14.5 mmol. Decomposition temperature: 173.8° C. (DTA onset), 177.8° C. (TGA, weight loss: 86.4%) density: 1.73 g/cm³ at 20° C.

Example 4

Ammonium tetrakis(3,5-dinitro-1H-1,2,4-triazolyl)borate: A 150 mL glass ampule equipped with a grease free high-vacuum PTFE valve and a TEFLON™ coated stir bar was flamed-out under vacuum. Inside the dry-box, the ampule was loaded with 1.18 g (8.00 mmol) 3,5-dinitro-1H-1,2,4-triazole and 61.6 mg (2.00 mmol) ammonia borane. The ampule was connected to a vacuum line, evacuated and cooled to –196° C. About 10 mL of dry dimethoxyethane was slowly condensed into the ampule. The ampule was closed and allowed to warm to ambient temperature. After 30 minutes, the ampule was heated to 110° C. for eight hours. The obtained yellow solution was cooled to −196° C. and 5.9 mmol of evolved hydrogen was pumped off. The reaction mixture was allowed to warm to ambient temperature. Subsequent evacuation to a constant weight over 24 hours resulted in a yellow solid of ammonium tetrakis(3,5-dinitro-1H-1,2,4-triazolyl)borate, 8.0 mmol.

Example 5

Sodium tetrakis(5-nitro-2H-tetrazolyl)borate: A 150 mL glass ampule equipped with a grease free high-vacuum PTFE valve and a TEFLON™ coated stir bar was flamed-out under vacuum. Inside the dry-box, the ampule was loaded with 460 mg (4.00 mmol) 5-nitro-2H-tetrazole and 37.8 mg (1.00 mmol) sodium borohydride. The ampule was connected to a vacuum line, evacuated and cooled to −196° C. About 5 mL of dry dimethoxyethane was slowly condensed into the ampule. The ampule was closed and allowed to warm to ambient temperature. As soon as the solvent melted and contacted the solid mixture at the bottom of the ampule, gas evolution started. The mixture was then stirred for about 30 minutes at ambient temperature. The clear, light yellow solution was cooled to −196° C., and the evolved hydrogen pumped off. The ampule was closed off and heated to 60° C. while stirring. After 3 hours, an orange solution was obtained and the temperature was raised to 80° C. After 24 hours, the solution was allowed to cool to ambient temperature and then cooled to −196° C., the evolved hydrogen pumped off and the reaction mixture allowed to warm to ambient temperature. Subsequent evacuation to a constant weight over 24 hours resulted in a yellow solid of sodium tetrakis(5-(trinitromethyl)-2H-tetrazolyl)borate, 1.0 mmol.

Example 6

Ammonium tetrakis(5-nitro-2H-tetrazolyl)borate: A 150 mL glass ampule equipped with a grease free high-vacuum PTFE valve and a TEFLON™ coated stir bar was flamed-out under vacuum. Inside the dry-box, the ampule was loaded with 920 mg (8.00 mmol) 5-nitro-2H-tetrazole and 61.6 mg (2.00 mmol) ammonia borane. The ampule was connected to a vacuum line, evacuated and cooled to −196° C. About 10 mL of dry dimethoxyethane was slowly condensed into the ampule. The ampule was closed and allowed to warm to ambient temperature. After 30 minutes, the ampule was heated to 110° C. for eight hours. The obtained yellow solution was cooled to −196° C. and the evolved hydrogen was pumped off. The reaction mixture was allowed to warm to ambient temperature. Subsequent evacuation to a constant weight over 24 hours resulted in a yellow solid of ammonium tetrakis(5-nitro-2H-tetrazolyl)borate, 8.0 mmol.

Example 7

Sodium tetrakis(5-(trinitromethyl)-2H-tetrazolyl)borate: A 150 mL glass ampule equipped with a grease free high-vacuum PTFE valve and a TEFLON™ coated stir bar was flamed-out under vacuum. Inside the dry-box, the ampule was loaded with 876 mg (4.00 mmol) 5-(trinitromethyl)-2H-tetrazole and 37.8 mg (1.00 mmol) sodium borohydride. The ampule was connected to a vacuum line, evacuated and cooled to −196° C. About 5 mL of dry dimethoxyethane was slowly condensed into the ampule. The ampule was closed and allowed to warm to ambient temperature. As soon as the solvent melted and contacted the solid mixture at the bottom of the ampule gas evolution started. The mixture was then stirred for about 30 minutes at ambient temperature. The clear, light yellow solution was cooled to −196° C., and the evolved hydrogen pumped off. The ampule was closed off and heated to 60° C. while stirring. After 3 hours, an orange solution was obtained and the temperature was raised to 80° C. After 24 hours, the solution was allowed to cool to ambient temperature and then cooled to −196° C., the evolved hydrogen pumped off and the reaction mixture allowed to warm to ambient temperature. Subsequent evacuation to a constant weight over 24 hours resulted in a yellow solid of sodium tetrakis(5-(trinitromethyl)-2H-tetrazolyl)borate, 1.0 mmol.

Example 8

Ammonium tetrakis(5-(trinitromethyl)-2H-tetrazolyl)borate: A 100 mL glass ampule equipped with a grease free high-vacuum PTFE valve and a TEFLON™ coated stir bar was flamed-out under vacuum. Inside the dry-box, the ampule was loaded with 896 mg (4.00 mmol) 5-(trinitromethyl)-2H-tetrazole and 30.8 mg (1.00 mmol) ammonia borane. The ampule was connected to a vacuum line, evacuated and cooled to −196° C. About 10 mL of dry dimethoxyethane was slowly condensed into the ampule. The ampule was closed and allowed to warm to ambient temperature. After 30 minutes, the ampule was heated to 100° C. for eight hours. The obtained yellow solution was cooled to −196° C. and the evolved hydrogen was pumped off. The reaction mixture was allowed to warm to ambient temperature. Subsequent evacuation to a constant weight over 24 hours resulted in a yellow solid of ammonium tetrakis(5-(trinitromethyl)-2H-tetrazolyl)borate, 4.0 mmol.

Example 9

Sodium tetrakis(2,3,5-trinitro-1H-imidazolyl)borate: A 150 mL glass ampule equipped with a grease free high-vacuum PTFE valve and a TEFLON™ coated stir bar was flamed-out under vacuum. Inside the dry-box, the ampule was loaded with 812 mg (4.00 mmol) 2,3,5-trinitro-1H-imidazole and 37.8 mg (1.00 mmol) sodium borohydride. The ampule was connected to a vacuum line, evacuated and cooled to −196° C. About 5 mL of dry dimethoxyethane was slowly condensed into the ampule. The ampule was closed and allowed to warm to ambient temperature. As soon as the solvent melted and contacted the solid mixture at the bottom of the ampule gas evolution started. The mixture was then stirred for about 30 minutes at ambient temperature. The clear, light yellow solution was cooled to −196° C., and the evolved hydrogen pumped off. The ampule was closed off and heated to 60° C. while stirring. After 3 hours, an orange solution was obtained and the temperature was raised to 120° C. After 24 hours, the solution was allowed to cool to ambient temperature and then cooled to −196° C., the evolved hydrogen pumped off and the reaction mixture allowed to warm to ambient temperature. Subsequent evacuation to a constant weight over 24 hours resulted in a yellow solid of sodium tetrakis(2,3,4-trinitro-1H-imidazolyl)borate, 1.0 mmol.

Example 10

Ammonium tetrakis(2,3,5-trinitro-1H-imidazolyl)borate: A 150 mL glass ampule equipped with a grease free high-vacuum PTFE valve and a TEFLON™ coated stir bar was flamed-out under vacuum. Inside the dry-box, the ampule was loaded with 1.62 g (8.00 mmol) 2,3,5-trinitro-1H-imidazole and 61.6 mg (2.00 mmol) ammonia borane. The ampule was connected to a vacuum line, evacuated and cooled to −196° C.

About 10 mL of dry dimethoxyethane was slowly condensed into the ampule. The ampule was closed and allowed to warm to ambient temperature. After 30 minutes, the ampule was heated to 110° C. for eight hours. The obtained yellow solution was cooled to −196° C. and the evolved hydrogen was pumped off. The reaction mixture was allowed to warm to ambient temperature. Subsequent evacuation to a constant weight over 24 hours resulted in a yellow solid of ammonium tetrakis(2,3,5-trinitro-1H-imidazolyl)borate, 8.0 mmol.

Example 11

Sodium tetrakis(2,3,4-trinitro-1H-pyrazolyl)borate: A 150 mL glass ampule equipped with a grease free high-vacuum PTFE valve and a TEFLON™ coated stir bar was flamed-out under vacuum. Inside the dry-box, the ampule was loaded with 812 mg (4.00 mmol) 2,3,4-trinitro-1H-pyrazole and 37.8 mg (1.00 mmol) sodium borohydride. The ampule was connected to a vacuum line, evacuated and cooled to −196° C. About 5 mL of dry dimethoxyethane was slowly condensed into the ampule. The ampule was closed and allowed to warm to ambient temperature. As soon as the solvent melted and contacted the solid mixture at the bottom of the ampule gas evolution started. The mixture was then stirred for about 30 minutes at ambient temperature. The clear, light yellow solution was cooled to −196° C., and the evolved hydrogen pumped off. The ampule was closed off and heated to 60° C. while stirring. After 3 hours, an orange solution was obtained and the temperature was raised to 120° C. After 24 hours, the solution was allowed to cool to ambient temperature and then cooled to −196° C., the evolved hydrogen pumped off and the reaction mixture allowed to warm to ambient temperature. Subsequent evacuation to a constant weight over 24 hours resulted in a yellow solid of sodium tetrakis(2,3,4-trinitro-1H-pyrazolyl)borate, 1.0 mmol.

Example 12

Ammonium tetrakis(2,3,4-trinitro-1H-pyrazolyl)borate: A 150 mL glass ampule equipped with a grease free high-vacuum PTFE valve and a TEFLON™ coated stir bar was flamed-out under vacuum. Inside the dry-box, the ampule was loaded with 1.62 g (8.00 mmol) 2,3,4-trinitro-1H-pyrazole and 61.6 mg (2.00 mmol) ammonia borane. The ampule was connected to a vacuum line, evacuated and cooled to −196° C. About 10 mL of dry dimethoxyethane was slowly condensed into the ampule. The ampule was closed and allowed to warm to ambient temperature. After 30 minutes, the ampule was heated to 110° C. for eight hours. The obtained yellow solution was cooled to −196° C. and the evolved hydrogen was pumped off. The reaction mixture was allowed to warm to ambient temperature. Subsequent evacuation to a constant weight over 24 hours resulted in a yellow solid of ammonium tetrakis(2,3,4-trinitro-1H-pyrazolyl)borate, 8.0 mmol.

Example 13

Potassium tetrakis(3,5-dinitro-1H-1,2,4-triazolyl)aluminate: Inside a dry-box, a 200 mL glass ampule that was equipped with a grease free high-vacuum PTFE valve and a TEFLON™ coated stir bar was charged with 1.703 g (10.71 mmol) 3,5-dinitro-1H-1,2,4-triazole and 703.7 mg (3.570 mmol) potassium 3,5-dinitro-1H-1,2,4-triazolate. The ampule was connected to a vacuum line, evacuated and cooled to −196° C. About 15 mL of anhydrous dimethoxyethane was condensed into the ampule. The ampule was closed and allowed to warm to ambient temperature. When all solid was dissolved, the clear, yellow solution was cooled to −196° C., and 257 mg (3.570 mmol) trimethylaluminum was condensed into the ampule. The mixture was allowed to warm to ambient temperature. After 16 hours, a red solution was obtained. Subsequent pumping at ambient temperature to a constant weight over 24 hours resulted in an orange solid of potassium tetrakis(3,5-dinitro-1H-1,2,4-triazolyl)aluminate, 3.57 mmol. Decomposition temperature: 172.6° C. (TGA, weight loss: 83.0%).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A highly energetic, high-oxygen carrier suitable as high-performing green replacement for ammonium perchlorate, the high-oxygen carrier comprising:
   a halogen-free ionic salt having a fuel cation and an over-oxidized anion described by formula I:

wherein:
   $X_1, X_2, X_3, X_4$ are each independently C—R or N;
   R is H, $NO_2$ or —$C(NO_2)_3$ with the proviso that 0, 1, 2, or 3 of $X_1, X_2, X_3, X_4$ are N and at least one of $X_1, X_2, X_3, X_4$ includes $NO_2$ or $C(NO_2)_3$; and
   M is boron, aluminum, or gallium, the carrier having sufficient amounts of oxygen for complete or near complete combustion of the over-oxidized anion, the fuel cation, metal additives and binders.

2. The high-oxygen carrier of claim 1 wherein M is boron.

3. The high-oxygen carrier of claim 1 wherein the M is aluminum.

4. The high-oxygen carrier of claim 1 wherein the over-oxidized anion includes a nitro-substituted azolyl ligand selected from the group consisting of 3,5-dinitro-1H-1,2,4-triazolyl, 5-nitro-3-(trinitromethyl)-1H-1,2,4-triazolyl, 5-(trinitromethyl)-2H-tetrazolyl, 5-nitro-2H-tetrazolyl, 3,4,5-trinitro-1H-pyrazolyl, 2,4,5-trinitro-1H-imidazolyl, and combinations thereof.

5. The high-oxygen carrier of claim 1 wherein the cation is selected from the group consisting of $NH_4^+$, $N_2H_5^+$, $N_2H_6^{2+}$, $NH_3OH^+$, and $H_2NC(NH_2)NH_2^+$.

6. The high-oxygen carrier of claim 5 wherein the anion is tetrakis(3,5-dinitro-1H-1,2,4-triazolyl)borate.

7. The high-oxygen carrier of claim 5 wherein the anion is tetrakis(5-nitro-3-(trinitromethyl)-1H-1,2,4-triazolyl)borate.

8. The high-oxygen carrier of claim 5 wherein the anion is tetrakis(5-(trinitromethyl)-2H-tetrazolyl)borate.

9. The high-oxygen carrier of claim 5 wherein the anion is tetrakis(5-nitro-2H-tetrazolyl)borate.

10. The high-oxygen carrier of claim 5 wherein the anion is tetrakis(3,4,5-trinitro-1H-pyrazolyl)borate.

11. The high-oxygen carrier of claim 5 wherein the anion is tetrakis(2,4,5-trinitro-1H-imidazolyl)borate.

12. The high-oxygen carrier of claim 5 wherein the anion is tetrakis(5-nitro-2H-tetrazolyl)borate.

13. The high-oxygen carrier of claim 5 wherein the anion is tetrakis(5-(trinitromethyl)-2H-tetrazolyl)borate.

14. The high-oxygen carrier of claim 5 wherein the anion is tetrakis(3,5-dinitro-1H-1,2,4-triazolyl)aluminate.

15. The high-oxygen carrier of claim 5 wherein the anion is tetrakis(5-nitro-3-(trinitromethyl)-1H-1,2,4-triazolyl)aluminate.

16. The high-oxygen carrier of claim 5 wherein the anion is tetrakis(5-(trinitromethyl)-2H-tetrazolyl)aluminate.

17. The high-oxygen carrier of claim 5 wherein the anion is tetrakis(5-nitro-2H-tetrazolyl)aluminate.

18. The high-oxygen carrier of claim 5 wherein the anion is tetrakis(3,4,5-trinitro-1H-pyrazolyl)aluminate.

19. The high-oxygen carrier of claim 5 wherein the anion is tetrakis(2,4,5-trinitro-1H-imidazolyl)aluminate.

20. The high-oxygen carrier of claim 5 wherein the anion is tetrakis(5-nitro-2H-tetrazolyl)aluminate.

21. The high-oxygen carrier of claim 5 wherein the anion is tetrakis(5-(trinitromethyl)-2H-tetrazolyl)aluminate.

22. A method of preparing highly energetic, high-oxygen carriers, the method comprising:
reacting a metal or semimetal compound including a moiety having formula $ML_n$ with a nitro-substituted azole having formula II

II to form a first salt having a first cation and an over-oxidized anion described by formula I such that molecular hydrogen or a $C_{1-12}$ alkane is evolved:

(I)

wherein:
$X_1, X_2, X_3, X_4$ are each independently C—R or N;
R is H, $NO_2$ or —$C(NO_2)_3$ with the proviso that 0, 1, 2, or 3 of $X_1, X_2, X_3, X_4$ are N and at least one of $X_1, X_2, X_3, X_4$ includes $NO_2$ or $C(NO_2)_3$;
M is boron, aluminum, or gallium;
L are independently a hydrogen atom or a $C_{1-12}$ alkyl ligand; and
n is 1 to 4.

23. The method of claim 22 wherein the metal or semimetal compound includes boron or aluminum.

24. The method of claim 22 wherein the metal or semimetal compound includes boron.

25. The method of claim 22 wherein the metal or semimetal compound includes aluminum.

26. The method of claim 22 wherein the metal or semimetal compound includes $BH_4^-$.

27. The method of claim 26 wherein the metal or semimetal compound is an alkali metal $BH_4^-$ salt.

28. The method of claim 27 wherein the alkali metal $BH_4^-$ salt includes an alkali metal selected from the group consisting of lithium, sodium, potassium.

29. The method of claim 22 wherein the metal or semimetal compound is ammonia borane.

30. The method of claim 22 wherein the metal or semimetal compound is reacted with the nitro-substituted azoles in a solvent that includes alkyl ethers.

31. The method of claim 30 wherein the solvent is 1-methoxy-2-(2-methoxyethoxy)ethane (diglyme).

32. The method of claim 31 wherein the metal or semimetal compound is an alkali metal borohydride.

33. The method of claim 22 wherein the metal or semimetal compound is an alkali metal borohydride.

34. The method of claim 22 wherein the first salt is an alkali metal tetrakis-nitroazolylborate salt.

35. The method of claim 34 wherein the alkali metal tetrakis-nitroazolylborate salt is contacted with an ion-exchange resin to form an ammonium salt.

36. The method of claim 34 wherein the alkali metal tetrakis-nitroazolylborate salt is reacted by double ion-exchange metathesis to form an ammonium salt.

37. The method of claim 22 wherein ammonia borane is reacted with acidic hydrogen atoms of nitroazoles under dihydrogen evolution to form an ammonium tetrakis-nitroazolylborate salt.

38. A method for forming an ammonium tetrakis-nitroazolylborate salt comprising reacting a tris-nitroazolyl borane having formula III with an ammonium nitroazolate salt having formula IV:

III

IV wherein:
$X_1, X_2, X_3, X_4$ are each independently C—R or N;
R is H, $NO_2$ or —$C(NO_2)_3$ with the proviso that 0, 1, 2, or 3 of $X_1, X_2, X_3, X_4$ are N and at least of $X_1, X_2, X_3, X_4$ includes $NO_2$ or $C(NO_2)_3$; and
$M_1^+$ is an ammonium cation or a substituted ammonium cation.

* * * * *